US006586378B2

(12) United States Patent
Chandra

(10) Patent No.: US 6,586,378 B2
(45) Date of Patent: Jul. 1, 2003

(54) AQUEOUS HAIR STYLING COMPOSITIONS

(75) Inventor: Lalitesh Chandra, Merseyside (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 188 days.

(21) Appl. No.: 09/737,650

(22) Filed: Dec. 15, 2000

(65) Prior Publication Data

US 2001/0029242 A1 Oct. 11, 2001

(30) Foreign Application Priority Data

Dec. 20, 1999 (GB) ............................................... 9930104

(51) Int. Cl.$^7$ .............................. A61K 7/09; A61K 7/11; C11D 3/18; C11D 3/37
(52) U.S. Cl. ....................... 510/120; 510/122; 510/123; 510/127; 510/129; 424/70.1; 424/70.11; 424/70.15; 424/70.16; 424/70.17; 424/70.21; 424/70.22; 424/70.27; 424/70.31
(58) Field of Search ................................. 510/120, 122, 510/123, 127, 129; 424/70.1, 70.11, 70.15, 70.16, 70.17, 70.21, 70.22, 70.27, 70.31

(56) References Cited

U.S. PATENT DOCUMENTS

| | | | |
|---|---|---|---|
| 4,175,572 A | | 11/1979 | Hsiung et al. .................. 132/7 |
| 4,438,095 A | | 3/1984 | Grollier et al. ................ 424/70 |
| 4,520,008 A | | 5/1985 | Ando et al. .................... 424/47 |
| 5,384,118 A | * | 1/1995 | LaValle .................... 424/70.13 |
| 5,656,257 A | * | 8/1997 | Fealy et al. .............. 424/70.13 |

FOREIGN PATENT DOCUMENTS

| | | | | |
|---|---|---|---|---|
| CH | 676412 A5 | | 1/1991 | |
| DE | 19727903 C1 | * | 7/1998 | ............ A61K/7/06 |
| EP | 0035899 | | 9/1981 | |
| EP | 0376511 | | 7/1990 | |
| EP | 835647 A1 | * | 4/1998 | ............ A61K/7/00 |
| EP | WO 01/45651 A1 | * | 6/2001 | ............ A61K/7/06 |
| GB | 1033299 | | 6/1966 | |
| GB | 2206045 | | 12/1988 | |
| WO | 91/14418 | | 10/1991 | |
| WO | 98/31334 | | 7/1998 | |

OTHER PUBLICATIONS

International Search Report Application No. PCT/GB 00/04605 mailed Mar. 30, 2001.
Search Report under Section 17 Application No. GB 99/30104.6 dated Apr. 17, 2000.

* cited by examiner

Primary Examiner—Yogendra N. Gupta
Assistant Examiner—Brian P. Mruk
(74) Attorney, Agent, or Firm—Milton L. Honig

(57) ABSTRACT

An aqueous hair stying composition comprises:
(i) from 0.1% to 40%, by weight based on total weight, of oily or fatty material, the oily or fatty material including at least one material selected from hydrocarbon oils and glyceride fatty esters.
(ii) from 0.1% to 10%, by weight based on total weight, of a hair styling polymer;
(iii) from 0% to 30%, by weight based on total weight, of an aerosol propellant; and
(iv) from 0% to 5%, by weight based on total weight, of a surfactant.

The compositions have improved strength and durability of hair hold and superior sensory feel.

5 Claims, No Drawings

AQUEOUS HAIR STYLING COMPOSITIONS

FIELD OF THE INVENTION

This invention relates to aqueous hair styling compositions, for example creams, gels and especially aerosol hair styling mousses, which incorporate an oily or fatty material and which have improved strength and durability of hair hold and superior sensory feel.

BACKGROUND OF INVENTION AND PRIOR ART

Hair styling compositions such as hair styling mousses provide human hair with a temporary set which can be removed by water or by shampooing, and function by applying a thin film of a resin or gum onto the hair to adhere adjacent hairs together so that they retain the particular shape or configuration at the time of application.

Conventional hair styling mousses typically utilise a hair setting polymer, water, surfactant and propellant gas, with optional adjuvants such as aesthetic agents, fragrance and hair conditioning agents. The conditioning agents used have included silicone-type materials.

EP 0 523 388 discloses an aqueous hair styling aid or mousse composition incorporating a non-volatile silicone compound or other water-insoluble, emulsifiable conditioning agent. The preferred non-volatile silicone compound is a 3:1 mixture of a low molecular weight polydimethylsiloxane fluid and a higher molecular weight polydimethylsiloxane gum.

EP 0 205 306 discloses the use of high molecular weight silicone materials in styling mousses. These are defined as polydiorganosiloxanes having a viscosity of at least 100,000 cst. The high molecular weight silicone is dissolved in the propellant phase prior to filling the aerosol container.

A problem is that those silicone materials which are typically used as conditioning agents in hair care applications tend to make the hair too soft to form and retain a style.

The present inventors have surprisingly discovered that the strength and durability of hair hold delivered by a hair styling resin in an aqueous hair styling aid such as a hair styling mousse can be significantly increased by the inclusion in the formulation of certain oily or fatty materials. In particular, hair styling aids of the invention provide tough elastic films on the hair which spread more easily on hair to provide more sites for bonding than conventional styling aids. Advantageously, hair styling aids of the invention also exhibit superior sensory feel, in particular improved softness, shine and conditioning. Furthermore, compositions of the invention are able to protect hair against damage, and show a surprising benefit with respect to the reduction of split end formation.

DEFINITION OF THE INVENTION

The present invention provides an aqueous hair styling composition comprising:
(i) from 0.1% to 40%, by weight based on total weight, of oily or fatty material, the oily or fatty material including at least one material selected from hydrocarbon oils and glyceride fatty esters.
(ii) from 0.1% to 10%, by weight based on total weight, of a hair styling polymer;
(iii) from 0% to 30%, by weight based on total weight, of an aerosol propellant; and
(iv) from 0% to 5%, by weight based on total weight, of a surfactant.

DETAILED DESCRIPTION OF THE INVENTION (i) Oily or Fatty Material

Suitable oily or fatty materials for use in compositions of the invention will generally have a viscosity at ambient temperature of from $10^{-4}$ to 1.0 Pa.s, preferably from $10^{-3}$ to 0.5 Pa.s, more preferably from $5 \times 10^{-3}$ to 0.15 Pa.s as measured by a Carri-Med CSL2 100 controlled stress rheometer, from TA Instruments Inc.

The oily or fatty material in compositions of the invention includes at least one material selected from hydrocarbon oils and glyceride fatty esters.

Suitable hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 8 to about 19 carbon atoms. Branched chain hydrocarbon oils can and typically may contain higher numbers of carbon atoms, e.g. from about 5 up to about 70 carbon atoms, preferably from about 8 up to about 50 carbon atoms. Also suitable are polymeric hydrocarbons of alkenyl monomers, such as C2–C6 alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons, in which the number of carbon atoms per hydrocarbon molecule generally ranges from $C_{10}$ to $C_{40}$. Suitable commercially available materials of this type include Sirius M40 (carbon chain length $C_{10}$–$C_{30}$, viscosity $5.5 \times 10^{-3}$ Pa.s), Sirius M85 (carbon chain length $C_{10}$–$C_{40}$, viscosity $2.7 \times 10^{-2}$ Pa.s) and Sirius M340 (carbon chain length $C_{15}$–$C_{40}$, viscosity $1.5 \times 10^{-1}$ Pa.s), all available from Silkolene.

By "glyceride fatty esters" is meant the mono-, di-, and tri-esters formed between glycerol and long chain carboxylic acids such as $C_8$–$C_{22}$ carboxylic acids. A variety of these types of materials are present in vegetable and animal fats and oils, such as camellia oil, coconut oil, castor oil, safflower oil, sunflower oil, peanut oil, cottonseed oil, corn oil, olive oil, cod liver oil, almond oil, avocado oil, palm oil, sesame oil, lanolin and soybean oil. These have various ranges of carbon chain lengths depending on the source, typically between about 12 to about 18 carbon atoms. Synthetic oils include trimyristin, triolein and tristearin glyceryl dilaurate. Specific examples of preferred materials for inclusion in compositions of the invention as sources of glyceride fatty esters include camellia oil, coconut oil, sunflower oil, peanut oil, palm oil and soybean oil.

Other suitable oily or fatty materials which may be present in combination with the hydrocarbon oils and/or glyceride fatty esters in compositions of the invention include other fatty esters.

In general, fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, and mixtures thereof.

The monocarboxylic acid ester need not necessarily contain at least one chain with at least 10 carbon atoms, so long as the total number of aliphatic chain carbon atoms is at least 10. Examples include isopropyl myristate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of C4–C8 dicarboxylic acids such as C1–C22 esters (preferably C1–C6) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglyceryl polyfatty acid esters, ethoxylated glyceryl monostearate, 1,3-butylene glycol monostearate, 1,3-butylene glycol distearate, polyoxyethylene polyol fatty acid ester, sorbitan fatty acid esters and polyoxyethylene sorbitan fatty acid esters.

The oily or fatty material may be present in compositions of the invention as a single material or as a blend, provided that there is included at least one material selected from hydrocarbon oils and glyceride fatty esters as described above.

Blends are particularly preferred since these appear to give optimum benefits in respect of style longeveity and sensory feel.

Examples of blends which have been found useful in compositions of the invention are hydrocarbon oil/fatty ester blends and hydrocarbon oil/fatty ester/fatty ester blends. The hydrocarbon oil:fatty ester(s) weight ratio in such blends may suitably range from 1:0.01 to 0.01:1, preferably from 1:0.1 to 0.1:1, most preferably from 3:1 to 1:3. Specific examples of blends of this type include blends of mineral oil and soybean oil and blends of mineral oil, soybean oil and isopropyl myristate. Particularly preferred is a blend of mineral oil, soybean oil and isopropyl myristate, in which the mineral oil:soybean oil:isopropyl myristate weight ratio is 6:2:2.

Also suitable are fatty ester/fatty ester blends. A particularly preferred example of a blend of this type is a blend of isopropyl myristate and soybean oil, in which the isopropyl myristate:soybean oil weight ratio suitably ranges from 1:0.01 to 0.01:1, preferably from 1:0.1 to 0.1:1, most preferably from 2:1 to 1:2.

The total content of oily or fatty material in compositions of the invention suitably ranges from 1% to 25%, preferably from 5% to 15%, by total weight of oily or fatty material based on total weight of the composition.

(ii) Hair Styling Polymer

Hair styling polymers are well known articles of commerce and many such polymers are available commercially which contain moieties which render the polymers cationic, anionic, amphoteric or nonionic in nature. The polymers may be synthetic or naturally derived.

The amount of the polymer may range from 0.1 to 10%, preferably 0.5 to 6% by weight of the total composition.

Examples of anionic hair styling polymers are:
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, noctyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ® ES series available from ISP Corporation esterified copolymers of methyl vinyl ether and maleic anhydride).

Other suitable anionic hair styling polymers include carboxylated polyurethanes Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and polyurethane, having a CTFA designation PVP/polycarbamyl polyglycol ester. Suitable carboxylated polyurethane resins are disclosed in EP 0 619 111 A1 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-240 350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat®PQ11;
Polyquaternium-16 (formed from methylvinylimidazolium chloride and vinylpyrrolidone), available from BASF as Luviquat® 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally derived polymers include shellac, alginates, gelatins, pectins, starch, cellulose derivatives and chitosan or salts and derivatives thereof. Commercially available examples include Kytamer® (ex Amerchol) and Amaze® (ex National Starch).

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

Cationic hair styling polymers, such as Polyquaternium-11 and in particular Polyquaternium-16, are the preferred hair styling polymers in compositions of the invention.

(iii) Oily/Fatty Material:Hair Styling Polymer Ratios

The oily or fatty material (i) and the hair styling polymer (ii) are generally incorporated into compositions of the invention in a weight ratio (calculated on the basis of total oily/fatty material to total hair styling polymer in the composition) ranging from 1:1 to 30:1, preferably from 3:1 to 15:1, most preferably from 8:3 to 12:1.

(iv) Water

Compositions of the present invention will also include water, preferably distilled or deionised, as a solvent or carrier for the hair styling polymer and other components. Water will typically be present in amounts ranging from 30% to 98%, preferably from 60% to 95% by weight based on total weight.

Alcohol may optionally be employed as a co-solvent in compositions of the invention. A suitable alcohol is an aliphatic straight or branched chain monohydric alcohol having 2 to about 4 carbon atoms. Isopropanol and especially ethanol are preferred. A suitable level for the alcohol is up to 20%, preferably from 5% to 15%, by weight based on total weight.

(v) Product Form and Optional Ingredients

Compositions of the invention may suitably be in aerosol form or non-aerosol form. A particularly preferred product form is an aerosol hair styling mousse. Aerosol hair styling mousse compositions are emitted from the aerosol container as a foam which is then typically worked through the hair with fingers or a hair styling tool and either left on the hair or rinsed out.

Aerosol-form compositions of the invention will include an aerosol propellant (v) which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and isobutane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 30%, preferably from 2% to 30%, most preferably from 3% to 15% by weight based on total weight of the composition. If a propellant such as dimethyl ether includes a vapour pressure suppressant (e.g. trichloroethane or dichloromethane), for weight percentage calculations, the amount of suppressant is included as part of the propellant.

Aerosol hair styling mousses will typically also include one or more surfactants in a total amount ranging from 0.01% to 5%, preferably from 0.01% to 1%, most preferably from 0.02% to 0.8% by weight based on total weight.

Surfactants are generally classified as nonionic, anionic, cationic, amphoteric or zwitterionic according to their ionic behaviour in aqueous solution.

Examples of nonionic surfactants are condensation products of aliphatic (C8–C18) primary or secondary linear or branched chain alcohols or phenols with alkylene oxides, usually ethylene oxide and generally having from 3 to 30 ethylene oxide groups. Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates.

Examples of anionic surfactants are the alkyl sulphates, alkyl ether sulphates, alkaryl sulphonates, alkanoyl isethionates, alkyl succinates, alkyl sulphosuccinates, Nalkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of cationic surfactants are cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

Preferred surfactants for use in aerosol hair styling mousses according to the invention are nonionic surfactants such as polysorbate 20, polysorbate 80, ethoxylated nonylphenol, steareth-20, cetosteareth-20, steareth-30, cetosteareth-30, steareth-50, cetosteareth-50, and mixtures thereof. Surfactants selected from anionic, cationic, amphoteric and zwitterionic surfactants may suitably be used in conjunction with any of the above nonionic surfactants, to improve, for example, foaming power and/or foam stability.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream, leave-on conditioner or gel.

Such a cream, leave-on conditioner or gel will typically include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid cross-linked with polyallylsucrose as described in U.S. Pat. No. 2,798,053. These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

(vi) Further Optional Ingredients

Compositions of this invention may contain any other ingredient normally used in hair treatment formulations. These other ingredients may include, viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

The invention is further illustrated by way of the following Examples, in which all percentages are by weight based on total weight unless otherwise stated.

EXAMPLES

The following Examples illustrate formulations according to the invention.

| Ingredient % active | Ex 1 | Ex 2 | Ex 3 | Ex 4 | Ex 5 | Ex 6 | Ex 7 | Ex 8 |
|---|---|---|---|---|---|---|---|---|
| GAFQUAT® 734 | 3 | 3 | 3 | | | | | |
| LUVIQUAT® FC550 | | | | 3 | 3 | 3 | 3 | 3 |
| Sirius M85 mineral oil | 10 | | | 6 | | 6 | 6 | 6 |
| Polybutene | | 10 | | | | | | |
| Peanut Oil | | | 6 | | | | | |
| Soya Oil | | | | | 10 | 2 | 2 | 2 |
| Isopropyl myristate | | | | | | 2 | 2 | 2 |
| Polysorbate 80 | 0.3 | 0.3 | 0.3 | 0.3 | 0.3 | 0.3 | | |
| Polyoxyethylene (15) lauryl ether | | | | | | | 1 | 1 |
| Ethanol | 8 | 8 | 8 | 8 | 8 | 8 | 8 | |
| Water | q.s. | q.s. | q.s. | q.s. | q.s. | q.s. | q.s. | q.s. |

Evaluation

The formulations of Examples 1 to 9 were evaluated for switch longevity as follows:

A permed 10 g switch was shampooed and then treated with 0.1 g of test formulation. The switch was then styled to create waviness and left to dry. Thereafter, the switch was finger combed 10 times after the first hour and its increase in volume compared with a switch treated with a control formulation in which the oil ingredients were omitted. Visual measurements of switch volume were made every hour up to 5 hours after treatment without any further finger combing.

The switch test results indicated that in terms of longevity of the style and sensory properties the presence of oil was advantageous. Presence of 10% blended oil in the formulation (Examples 6 to 8) gave optimum benefit for style longevity and feel properties.

Instrumental measurements indicated that the oil helps spread the styling polymer on hair giving larger area coverage and thinner film.

What is claimed is:

1. An aqueous hair styling composition comprising:
   (i) from 0.1% to 40%, by weight based on total weight, of an oily or fatty material, wherein the oily or fatty material is a blend of mineral oil, soybean oil, and isopropyl myristate;
   (ii) from 0.1% to 10%, by weight based on total weight, of a hair styling polymer;
   (iii) from 0% to 30%, by weight based on total weight, of an aerosol propellant; and
   (iv) from 0% to 5%, by weight based on total weight, of a surfactant.

2. A composition according to claim 1, in which the total content of oily or fatty material ranges from 5% to 15%, by total weight of oily or fatty material based on total weight of the composition.

3. A composition according to claim 1, in which the hair styling polymer is a cationic hair styling polymer.

4. A composition according to claim 1, in which the weight ratio of the total oily or fatty to total hair styling polymer in the composition ranges from 8:3 to 12:1.

5. A composition according to claim 1, which is in the form of an aerosol hair styling mousse including one or more surfactants in a total amount ranging from 0.02% to 0.8% by weight based on total weight.

* * * * *